United States Patent [19]

Nohso

[11] Patent Number: 4,890,930

[45] Date of Patent: * Jan. 2, 1990

[54] AUTOMATIC SAMPLING APPARATUS

[75] Inventor: Hidenori Nohso, Kakogawa, Japan

[73] Assignee: Mitsubishi Chemical Industries Limited, Tokyo, Japan

[*] Notice: The portion of the term of this patent subsequent to May 21, 2002 has been disclaimed.

[21] Appl. No.: 142,953

[22] Filed: Jan. 12, 1988

[30] Foreign Application Priority Data

Jan. 16, 1987 [JP] Japan .................................. 62-7555

[51] Int. Cl.⁴ .............................................. B01F 9/00
[52] U.S. Cl. ..................................... 366/208; 422/63; 422/65; 422/99
[58] Field of Search ............... 366/219, 142, 208, 140, 366/202, 209, 210, 211; 422/63, 65, 67, 72, 99, 104

[56] References Cited

U.S. PATENT DOCUMENTS 4,518,264  5/1985  Nohso ................................ 366/208
4,713,974 12/1987  Stone ..................................... 422/67

Primary Examiner—Robert W. Jenkins
Attorney, Agent, or Firm—Oblon, Spivak, McClelland, Maier & Neustadt

[57] ABSTRACT

In an automatic sample supply apparatus which holds a plurality of sample vessels in a waiting station in a matrix pattern and which includes a plurality of rows of sample vessels, sends out the sample vessels in the front row laterally one by one to a sampling station, returns the sample vessels which have finished the required treatment to the waiting station, and advances the sample vessels in the rearmost row in the waiting station collectively as a whole in one step corresponding to one row when all the sample vessels in the front row of the waiting station have been sent out, a suction needle for drawing up the sample in a sample vessel which can penetrate a rubber stopper secured to the sample vessels is employed.

5 Claims, 7 Drawing Sheets

AUTOMATIC SAMPLING APPARATUS

BACKGROUND OF THE INVENTION

1. Field of the Invention

This invention relates to an automatic sample supply apparatus which sequentially supplies to and returns from a station for analysis or other treatment a plurality of sample vessels such as test tubes. more particularly, this invention relates to an automatic sample supply apparatus as mentioned above in which rubberstoppered sample vessels can be used and samples therein can be drawn out by a suction needle means with the rubber stopper retained in position. In this specification, the term "sampling" means drawing out liquid test samples from sample vessels and supplying the samples to an analytical apparatus, for example a vessel for analysis such as an optical cell.

2. Description of the Prior Art

U.S. Pat. No. 4,518,264, for instance, discloses an automatic sample supply apparatus which sequentially supplies to and returns from a station for analysis a plurality of sample vessels such as test tubes. In this apparatus, a plurality of test tubes, respectively accommodated in a magazine, are arranged in a waiting station, forwarded to a stirring station one by one, and then the empty vessels are returned to the waiting station after the analysis or other treatment has been finished.

In this known automatic sample supply apparatus, a plurality of test tubes are arranged upright in a matrix pattern comprised of a plurality of rows of sample vessels in a waiting station. The waiting station is provided with a means which advances a row of sample vessels as a whole in the direction of the column one row at a time and a means which feeds test tubes in the front row laterally one by one to a sample transfer means through an outlet gate provided at one end of the front row, said sample transfer means transfering the sample vessel to a stirring station. The waiting station is further provided with an inlet gate for sample vessls at one end of the back row in the waiting station, via which emptied sample vessels are returned.

Each sample vessel sent out of the outlet gate of the waiting station is transfered to a stirring station by a transfer means, and the sample is stirred. After the sample has been stirred, the sample in the vessel is transfered to an analysis station by a suction tube which is inserted into the test tube for drawing up the sample, said suction tube being operated by the orders from the analysis station.

The suction tube is then withdrawn and the empty sample vessel is returned to the vicinity of the outlet gate by the transfer means, and is then passed through the inlet gate to the back row in the waiting station by a sample-forwarding means.

Such known apparatus is characterized in that the test samples can be stirred one by one, and therefore all the samples can be analyzed under the same conditions.

However, said apparatuses are not satisfactory because the samples vessels must be kept open so that a suction tube can be freely inserted therein, and therefore the samples are susceptible to contamination, deterioration, drying, etc. in such an apparatus. Usually, a large number at a time of samples are placed in the waiting station. Therefore, after they have been arranged in the waiting station, some samples must wait for one hour to one and half hour before they are subjected to analysis, during which time they are exposed to atmosphere and thus suffer the above-mentioned undesirable influences. Moreover, samples which readily vaporize or give off toxic fumes cannot be handled by these apparatuses, because the stoppers must be kept removed.

SUMMARY OF THE INVENTION

This invention provides, in an automatic sample supply apparatus which holds a plurality of sample vessels in a waiting station in a matrix pattern comprising a plurality of rows of sample vessels, sends out the sample vessels in the front row laterally one by one to a sampling station, returns the sample vessels which have finished the required treatment to the waiting station, and advances the sample vessels in the rearmost row in the waiting station collectively as a whole by one step corresponding to one row when all the sample vessels in the front row of the waiting station have been sent out, an improved apparatus which is provided with a suction needle for sampling the sample in a sample vessel which can penetratre a rubber stopper secured to the sample vessels.

In the automatic sample supply apparatus of the present invention, sample vessels are taken out one by one from one end of the front row of samples in the waiting station, shaken by a stirring device if necessary, and thus the sample is stirred, and drawn by a suction needle which is inserted into a sample vessel through the rubber stopper. After the needle is withdrawn, the vessel is returned to the back row in the waiting station. When all the vessels in one row have been sent out, the next row of sample vessels is advanced as a whole, and sample vessels in this next row are sent out.

In one aspect of the present invention, the suction needle is provided with a stopper means which prevents the sample vessel the rubber stopper of which is held by the suction needle from being lifted.

In another aspect of the present invention, the suction needle has a suction holes or holes on the side thereof.

In still another aspect of the present invention, the apparatus is combined with a device for stirring the samples.

BRIEF EXPLANATION OF THE DRAWINGS

A more complete appreciation of the invention and many of the attendant advantages thereof will be readily obtained as the same becomes better underfstood by reference to the following detailed description when considered in connection with the accompanying drawings, wherein.

DESCRIPTION OF THE PREFERRED EMBODIMENT

The embodiment described hereinafter represents an apparatus which holds 100 sample vessels (test tubes), i.e., samples taken from 100 persons for instance, in an arrangement marshalled in a waiting station, forwards them to a stirring station, and returns them to the initial waiting station. The term "sample vessel" used hereinafter means a vessel such as a test tube with its magazine whether it contains a sample such as blood or not.

Figure 1:
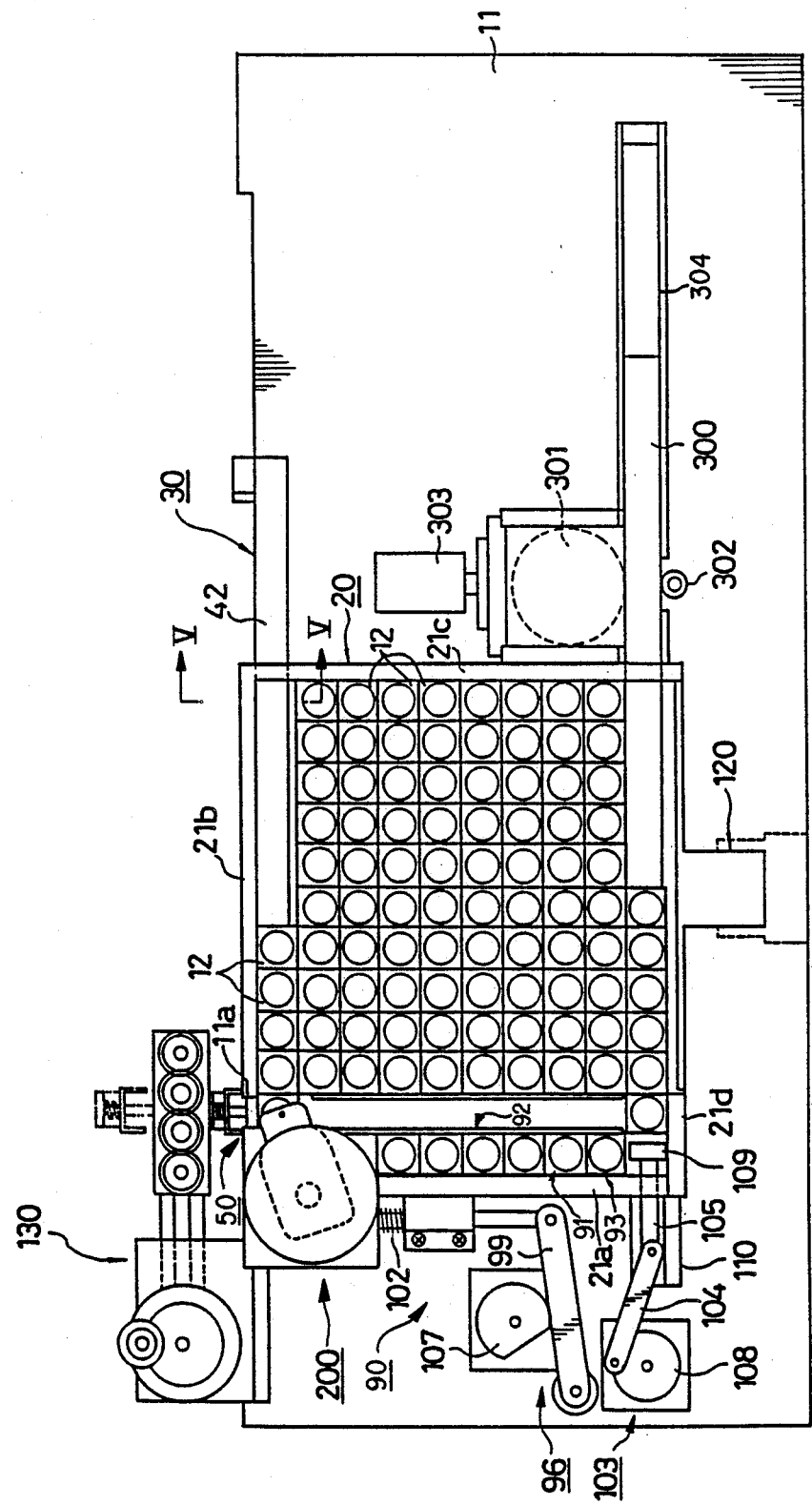
FIG. 1 is a plan view of the automatic sample supply appartus of one embodiment of the present invention.
Figure 5:
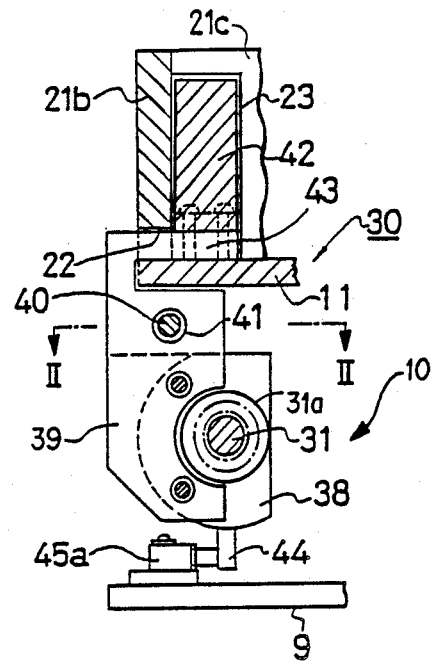
FIG. 5 is a cross-sectional view along the line V—V in FIG. 4.
Figure 7:
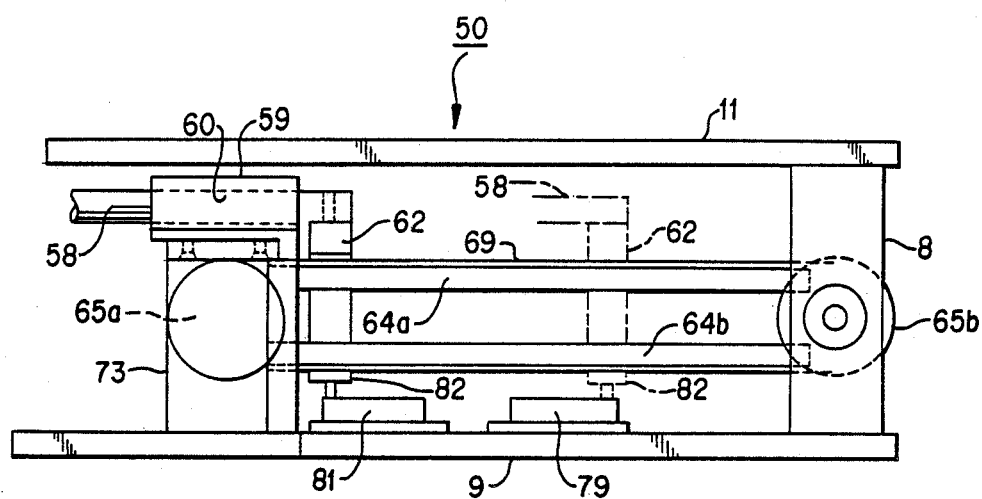
FIG. 7 is an enlarged side view along the line VII—VII in FIG. 4.

The automatic sample supply apparatus of this embodiment generally comprises a supporting plate 11 on which a waiting station 20, a send-out device 30, a sample-transferring device 50, a sample-forwarding device 90 and a sampling device 200 are provided as shown in FIG. 1. A sample-stirring device 130 is used in combination with this apparatus. The supporting plate 11 is supported on a base plate 9 via pillars 8 as shown in FIGS. 5 and 7.

Figure 2:
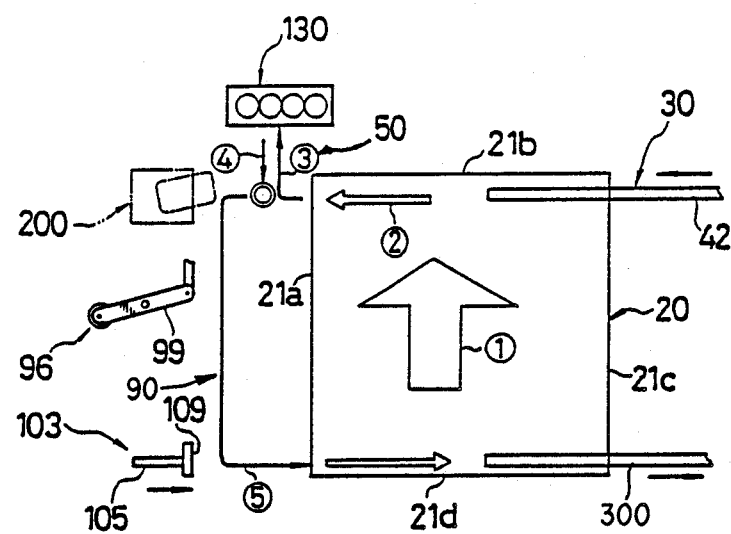
FIG. 2 is a partial plan view of the apparatus illustrating the movement of the sample vessels in the apparatus.

Before the structure of the apparatus is described in detail, the flow of sample vessels which are moved by various devices of the apparatus is explained by way of FIG. 2.

One hundred (100) sample vessels are marshalled in a 10×10 matrix pattern in a waiting station 20. A row of the sample vessels can be moved as a whole in the direction of arrow ①. At the front row, the sample vessels are sent out leftward (in the direction of arrow ②) one by one. Each sample vessel sent out is transferred to a stirring station (swinging device) 130 by means of the sample-transferring device 50 (in the direction of arrow ③. After the sample is stirred in the stirring station 130, the sample vessel is returned to the outlet gate of the waiting station (in the direction arrow ④. Here, a suction needle is inserted into the sample vessel penetrating through the rubber stopper and the sample liquid is drawn up. After the suction needle is withdrawn, the sample vessel is returned to the back row of the waiting station (in the direction of arrow ⑤.

The details of each component will be explained below.

On the supporting plate 11, rectangular side walls 21a–21d provide a waiting station receiving 100 sample vessels 12 arranged in a 10×10 matrix. The sample vessels in the front row (uppermost row in FIG. 1) in the waiting station are sent out laterally by means of the send-out device 30 on an intermittent basis one vessel at a time.

Figure 4:
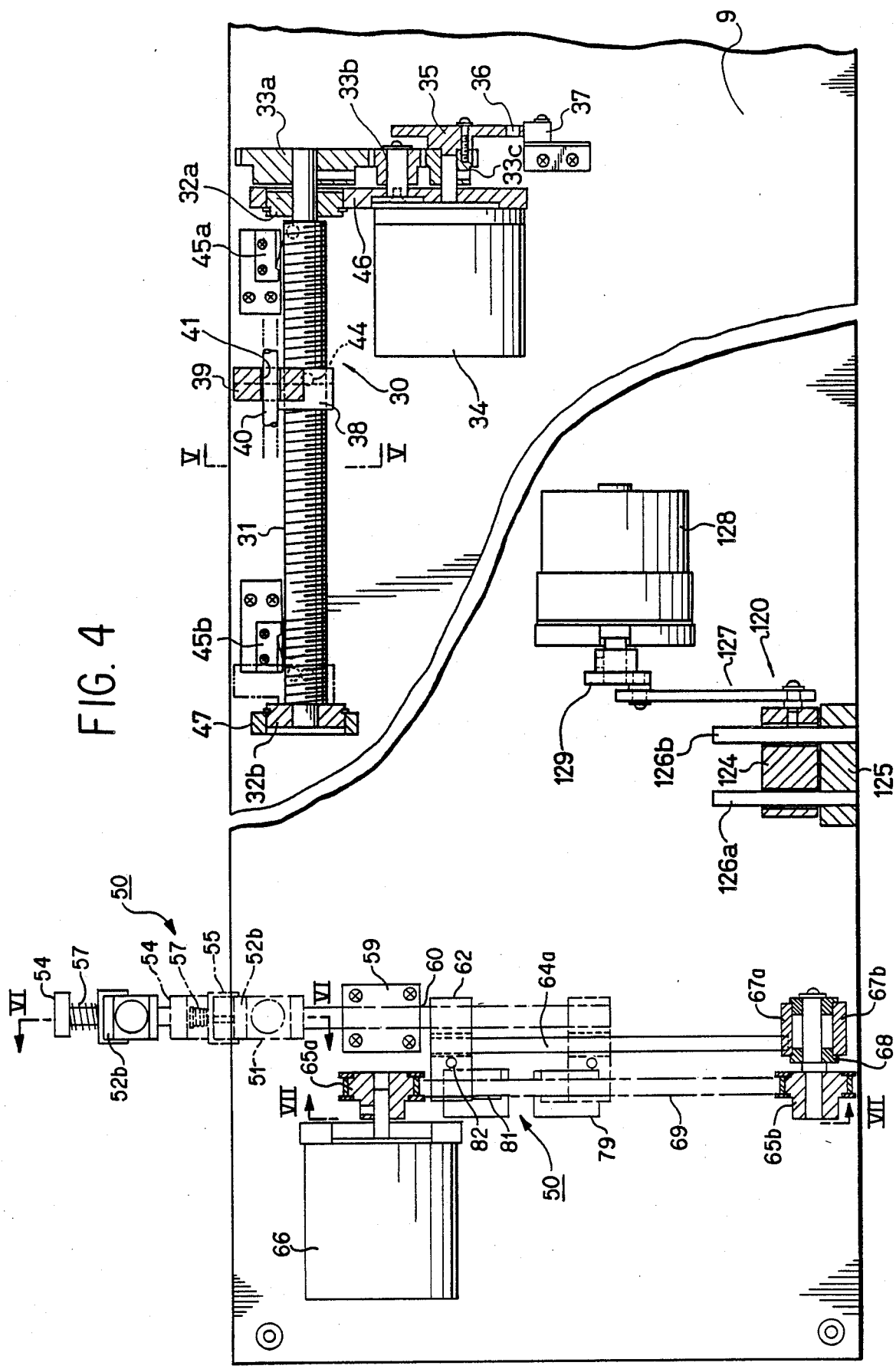
FIG. 4 is a plan view of the main part of the apparatus under the supporting plate illustrating the internal structure.

The main structure of this send-out device 30 is housed in a box provided underneath the supporting plate 11 as shown in FIG. 4. The send-out device 30 has a screw rod 31, which is provided in parallel with the front row of the matrix of the sample vessels near the edge of the supporting plate 11. The two ends thereof are provided with spindles (not coded), which are rotatably supported by bearings 32a and 32b. The right side end spindle is provided with a cogged wheel 33a, which meshes with an idle gear 33b. This idle gear 33b meshes with another gear 33c, which is secured to the driving shaft of a motor 34. To the gear 33c is secured a disk 35, which is provided with a protrusion 36 on the periphery thereof. The bearing 32a, gear 33b and the motor 34 are supported by a bracket 46, and the bearing 32b is supported by a bracket 47. This apparatus is provided with a control means, which is operated by the user. When the analytical apparatus is ready and the user actuates the control means, the driving motor 34 is actuated. In the vicinity of the disk 35, a limit switch means 37, which is turned off by the contact with the protrusion 36, is provided. When the gear 33c which is rotated by the motor 34 makes one revolution and the protrusion 36 of the disk 35 presses the limit switch 37 to stop the rotation of the motor 34, the screw rod 31 consequently rotates by the degree determined by the gear ratio of the gears 33a, 33b and 33c.

the screw rod 31 is provided with a slide-piece 38 engagedly mounted thereon. A supporter 39 having a recess avoiding the boss 31a provided in the slide-piece 38 is secured to the slide-piece 38 as shown in Figs.4 and 5. A guide rod 40 is provided in parallel with the screw rod 31 near the edge of the supporting plate 11. The supporter 39 is supported and guided by this guide rod 40 through a hole 41 provided therein. The upper end of the supporter extends to the upperside of the supporting plate 11 and forms an arm 43, which extends on the surface of the supporting plate 11 through a slit 22 provided in the side wall 21b of the waiting station over almost all the length thereof. A push-rod 42 is secured to the arm 43 of the supporter 39 on the upperside of the supporting plate 11.

The slide-piece 38 is provided with a protrusion 44 at the bottom thereof, which presses limit switch contacts 45a and 45b provided at the starting position and the end position of the slide piece 38. Thus, when the screw rod rotates, the push-rod is moved so as to send out sample test tubes one after another through the outlet gate 24 out of the waiting station 20.

Figure 3:
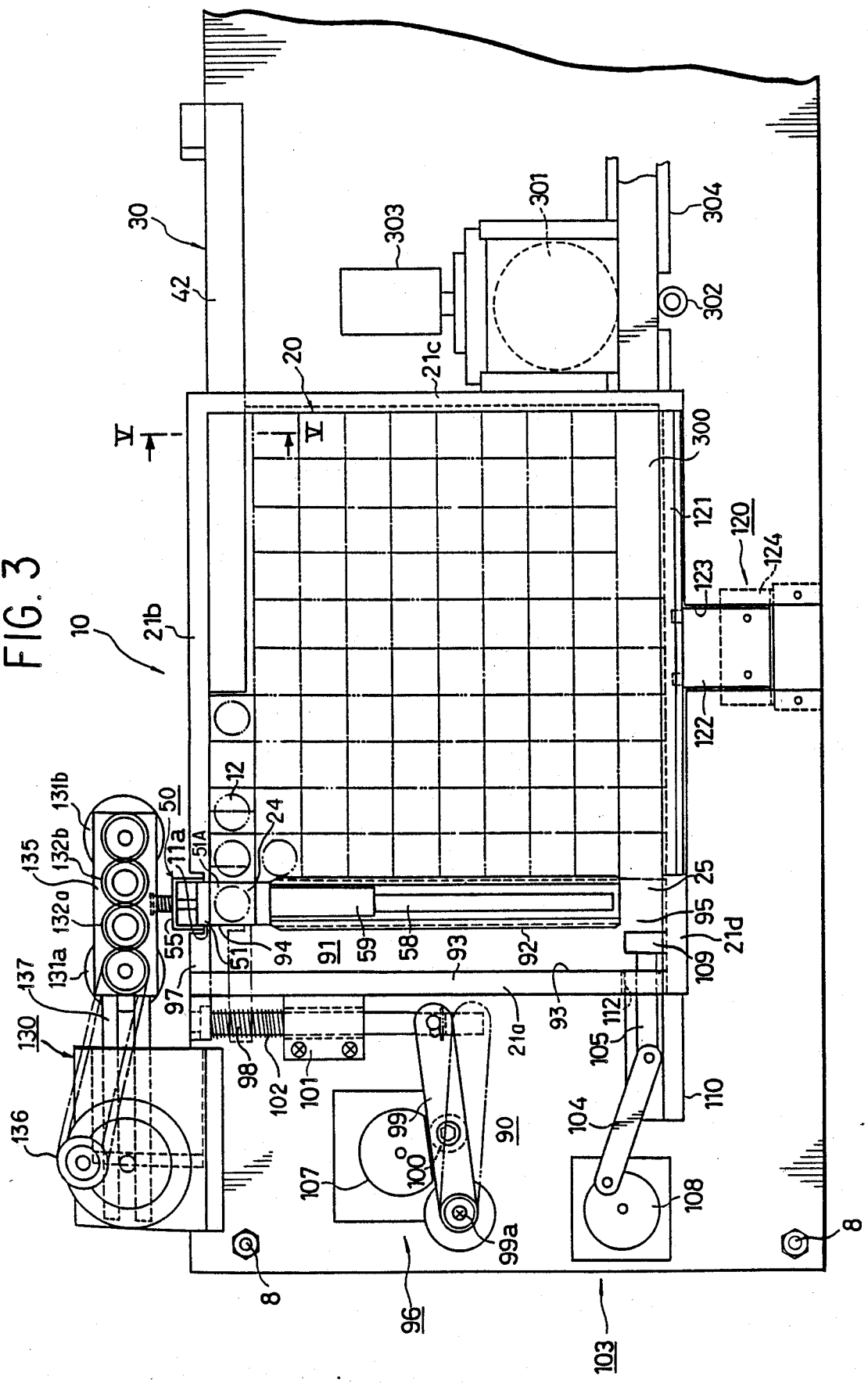
FIG. 3 is an enlarged plan view of the main part of the apparatus excepting showing part of the underside of the supporting plate.
Figure 6:
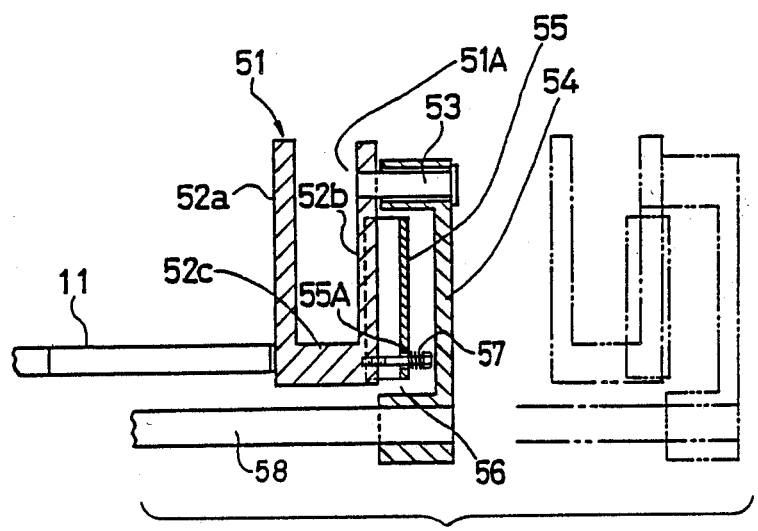
FIG. 6 is a cross-sectional view of the holder along the line VI—VI in FIG. 4.

The sample test tube thus sent-out is received by a sample holder 51 of the sample-transferring device 50 (FIG. 3). The holder 51 is illustrated in FIG. 6, which is a cross-sectional view along the line VI—VI in FIG. 4. The holder 51 is a U-shape piece comprising a pair of confronting walls 52a, 52b and a bottom 52c, and the upper end and the other confronting sides 51A are open. This holder 51 is swingably supported by a supporting member 54 secured to a supporting rod 58 (described in detail later) by means of a horizontal pivot 53 secured to one of the walls 52b.

The open sides 51A of the holder 51 are closable by means of a protective cover 55, which has a U-shaped horizontal cross section and is mounted on the holder 51 so as to encompass it. The protective cover 55 is merely for preventing a test tube held in the holder from dropping therefrom and has a length of slightly longer than half the height of the holder. A small screw rod 56 is secured to the side wall 52b of the holder, on which the protective cover 55 is freely mounted through a hole 55a provided therein, being pressed toward said side wall by means of a coil spring 57 mounted on said small screw rod held by a head member thereof. Thus the protective cover is biased to assume a position so as to close the openings 51A of the holder 51. The supporting member 54, which pivotably supports the holder 51 by means of a pivot 53, is secured to a supporting rod 58 at the lower end thereof. The supporting rod 58 extends under the supporting plate 11.

The supporting rod 58 can be moved forward and backward along its longitudinal axis. As shown in FIGS. 1 and 3, an indentation 11a is provided in the edge of the supporting plate 11 at a position close to the outlet gate 24 of the waiting station 20, and the holder 51 can freely enter therein and retired therefrom. When the holder 51 is completely received in the indentation 11a, the holder can receive a sample vessel (sample-receiving position). The width of the indentation 11a is approximately equal to the width of the holder 51. Therefore, when the holder 51 enters the indentation 11a, the protective cover 55 cannot enter the indentation 11a detained by the edge of the opening of the indentation 11a and thus the protective cover 55 is disengaged from the holder 51 pressing the coil spring 57. That is, the holder 51 is opened.

The holder 51 is designed so that the inside bottom surface 52c is at the same level as the upper surface of the supporting plate 11. Also, the depth of the indentation 11a is defined so as to correspond to the width of the openings 51A of the holder and the width of the outlet gate 24.

The supporting rod 58 extends passing through a bore 60 of a guide piece 59, which is secured to the base plate 9 as shown in FIG. 7. To the other end of the supporting rod 58 is secured a slide piece 62, which is slidably engaged with a first and a second guide rod 64a, 64b. In the vicinity of each one of these guide rods 64a, 64b, a timing pulley 65a, 65b is provided as shown in FIG. 4 and 7. The pulley 65a is secured to the driving shaft of a motor 66, and the pulley 65b is rotatably supported by a bearing 68, which is mounted on brackets 67a, 67b. A timing belt 69 having cogs on its inside surface is set up between the two timing pulleys 65a, 65b, and the above-mentioned slide piece 62 is secured to the upper side of the belt 69. Therefore, when the motor 66 rotates positively and reversely, the slide piece 62 moves forward and backward along the guide rods 64a, 64b, and thus the supporting rod 58 makes reciprocal motion.

by this movement of the supporting rod 58, the holder 51 stops at two positions, that is, a position where the holder 51 is received in the waiting station and receives or delivers a sample vessel sample-receiving position) and another position where the sample is stirred before sampling. In order to stop the holder 51 at the two positions, two limit switches 79, 81 which control the motor 66 are provided and the slide-piece 62 is provided with a protrusion 82 which presses the contacts of the limit switches 79, 81.

When the stirring of a sample is finished and the sample vessel is returned to the sample-receiving position and the sample is drawn out, the sample vessel is returned to the back row in the waiting station by means of the sample-forwarding means 90 (a first sample forwarding device and a second sample-forwarding device). This sample-forwarding device includes a return passage 91, which is provided on the upper surface of the supporting plate 11 and defined by side walls 92, 93 provided along the side wall 21a.

The front end of the wall 92 defining the return passage 91 does not reach the sample-receiving position and forms a port 94 confronting the outlet gate 24 (FIG. 3). The rear end of the return passage 91 turns at a right angle toward the waiting station. The rear ends of the side walls 92 and 93 do not reach the side wall 21d, and a second port 95 and an inlet gate 25 are formed.

The empty sample vessel placed in the sample-receiving position is moved to the port 94 of the return passage. The sample vessel placed in the front end of the return passage 91 is pushed toward the back row in the waiting station one vessel at a time by means of a first sample-forwarding device 96.

The first sample-forwarding device 96 has a push-arm 97 which extends to the return passage 91 through a horizontal slit provided at the front end of the side wall 93 (integral with side wall 21a). The waiting position of the push-arm 97 is at the side wall 21b so as not to prevent the entry of the sample vessel into the return passage 91 as shown in FIG. 3. The base end of the push-arm 97 is secured to an end of an operation rod 98 provided on the other side of the side wall 93 from the return passage 91 in parallel therewith slidably supported by a guide-piece 101 which is secured to the supporting plate 11. The other end of this operation rod 98 is pivotably connected to an end of an operation lever arm 99, which is arranged approximately at a right angle and pivotably secured to a vertical pin 99a. A cam disk 107, which is driven by a motor means (not shown), is provided in the vicinity of the operation lever arm 99, and comes into contact with a roller 100 which is rotatably secured to the underside of the operation lever arm 99. The cam disk has a straight line recess. The operation lever arm 99 is operated by these cam and roller.

FIG. 3 shows the first sample-forwarding device 96 including the operation lever 99 when the push-arm 97 is in the waiting position. The operation rod 98 slidably supported by a guide-piece 101 is energized by a coil spring 102 mounted on said rod between said guide piece 101 and a flange provided on the rod so as to tend toward the front end. When the cam disk 107 moves the operation lever arm 99 rearward, the push-arm 97 is moved rearward and the sample vessel placed in the front end of the return passage 91 is moved rearward.

Near the back row in the waiting station, a second sample forwarding device 103 is provided. The device 103 comprises a disk 108 driven by a motor (not shown), a crank arm 104 pivotably and excentrically connected to the disk 108 at one end, a rod 105 pivotably connected to the other end of the crank arm 104, and a push-piece 109 secured to the end of the rod 105 and a guide-rail 110 which guides the reciprocal motion of the rod 105.

The motors driving the cam disk 107 and the disk 108 are intermittently actuated so as to stop per every revolution. The rotation of the motors is controlled by limit switches provided in the vicinities of the cam disk 107 and the disk 108 the contacts of which are pressed by protrusions provided on the underside of the cam disk 107 and the disk 108 respectively.

The capacity of the return passage 91 is such that all the sample vessels placed in a row in the waiting station can be received. The empty sample vessels are returned rearward by the first sample-forwarding device 96 by the sample vessels being consecutively marshalled in the return passage and further returned to the back row in the waiting station by the second sample forwarding device 103. The front row becomes empty when its last sample vessel is received by the holder 51. Then the back row is put forward as a whole by means of a collective sample-forwarding device 120.

The collective sample-forwarding device 120 comprises a push plate 121 which is a part of the side wall 21d and a handle piece 122 secured to the push-plate 121, which is secured to a slide-piece 124 exposed from an opening 123 provided in the supporting plate 11 as shown in FIGS. 3 and 4. The slide-piece 124 is slidably mounted on two rods 126a, 126b, which are secured to the supporting plate 11 by means of a bracket block 125.

A connecting rod 127 is pivotably connected to the slide-piece 124 at one end thereof, and pivotably and excentrically fixed to a disk 129 rotated by a motor 128 at the other end. Therefore, when the disk 129 makes one revolution, the slide-piece 124 makes one reciprocal motion, and thus the push-plate 121 pushes the back row of the sample vessels forward by one row and returns to the initial position. Needless to say, the stroke is determined by the position where said other end of the connecting rod 127 is fixed to the disk 129.

Thus, when the sample vessels in the initial second row begin to be sent out by the send-out device 30 and transfered by the holder 51, the disk 108 is actuated and the rod 105 (push-piece 109) pushes the sample vessel standing at the rear end of the return passage 91 to the waiting position between the inlet port 95 and gate 25 and the the rod 105 is retired by the continued motion of the disk 108. Then, the cam disk 107 is actuated and the operation rod 98 moves so as to move the sample vessels marshalled in the return passage 91 rearward by one step corresponding to one vessel. Thus the front position of the return passage 91 is made vacant to receive the next sample vessel returned from the stirring position.

The above described cycle is repeated until all the sample vessels are handled.

The above-described device is usually in combination with a stirring device. A preferred stirring device is described in U.S. Pat. No. 4,518,264. Here the device is illustrated in FIG. 3 as 130. The device comprises two rotating disks or rollers 131a and 131b supported by a station board 135 associated by two idle cogged wheels 132a and 132b interposesd therebetween so that the two rollers rotate n the reverse direction. One of the rollers 131a is rotated by a rotating disk 136, which makes a circular motion per se, via a belt means. The station board 135 is slidable mounted on a rail 137 and linked with the rotating disk 136. Therefore, when the rotating disk 136 makes the circular motion as rotating per se, the rollers 131a, 131b collectively make reciprocal motion as rotating per se in the reverse direction.

When the motor 66 of the sample-transfering device 50 is actuated and the supporting rod 58 is put forward, a sample vessel held in the holder 51 is placed between the two rollers. In this case, the motion of the supporting rod 58 is controlled so that the holder 51 is inserted between the two rollers when the station board 135, that is, the rollers 131a, 131b, are in the neutral position and the insertion is not obstructed by the contact with the rollers. Once the holder 51 is inserted between the rollers 131a and 131b, the upper part of the test tube held by the holder 51 undergoes contact by the two rollers alternately. Thus the test tube is tilted around the pivot 53 by the contact with a roller in one orientation and rotated in one direction in one period and then tilted and rotated in the reverse orientation and direction at the next period. In this way, the sample is satisfactorily stirred. After the stirring device 130 is operated for a predetermined period of time, it is stopped. The device is controlled so that it stops at the neutral position. Then, the holder 51 is returned to the sample receiving position, where the sampling is carried out.

Figure 8:
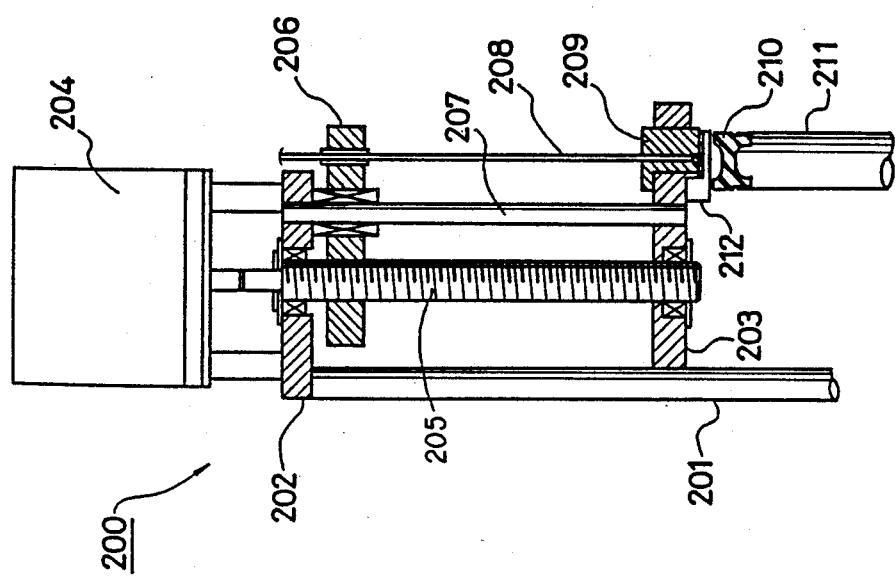
FIG. 8 is a partially cross-sectional side elevational view of the sampling device.

The sampling device 200 is illustrated in FIG. 8. The device comprises a pillar 201 secured to the base plate 9, two base boards 202 and 203 secured to the pillar 201 in a vertically spaced relation a motor 204 mounted on the upper base board 202, a vertical screw shaft 205 rotatably supported by the base boards 202 and 203, a nut piece 206 which is engagedly mounted on the screw shaft 205, a vertical guide rod 207 which is secured to the base boards 201 and 203 and serves as a guide for the nut piece 206, a suction needle 208 secured to the nut piece 206, a holding block 209 which is secured to the lower base board 209 and supports and guides the suction needle 208 and a stopper means 212 which is attached to the underside of the lower base board 203 and allows passage of the suction needle 208 but prevents the lifting of the test tube 211, the rubber stopper 210 of which is held by the suction needle 208 penetrating it. The upper part of the suction needle 208 is communicated to a suction means of an analysis apparatus by means of a flexible tubing although this is not illustrated. Also the holding block 209 is provided with a tubing which supplies a liquid for washing the outside of the suction needle 208 and sucking the used washing liquid, both the liquid supplied from the analysis apparatus to wash the inside of the needle and the liquid used to wash the outside. This sampling device is mounted on the supporting plate 11 so as to hang over the sample receiving position.

The test tubes used in the present apparatus are closed by a rubber stopper 210. When a sample vessel is returned from the stirring device 130 to the sample receiving position, the suction needle 208 is lowered by the positive rotation of the motor 204 and pricks and penetrates the rubber stopper 211 so as to draw up the sample in the test tube 211 (12). After a predetermined amount of the sample is drawn out, the drive of the motor 204 is reversed and the suction needle 208 is withdrawn. At this time, the test tube is lifted by the suction needle 208 which holds the rubber stopper 210. However, the lifting of the test tube is prevented by the stopper means 212 as mentioned above, and only the suction needle 208 is withdrawn.

After the sampling is finished, again the send-out device 30 operates to send out the empty sample vessel to the return passage 91 and the above described operation is continued.

At the back row in the waiting station 20, a rod 300 for preventing the test tubes from tumbling is inserted. The tumble-proof proof rod 300 is supported by a pair of guide rails 304, an idle roller 302 and a driving roller 301, which is driven by a motor 303. The tumble-proof rod 300 is used only when sample vessels in the back row are forwarded in the direction of the gate 24. Usually the tumble-proof rod 300 retires pushed by the sample vessels which are forwardly by the second sample forwarding device 103, when the motor 303 freely rotates.

In this manner, when all the sample vessels in the first front row are treated, the second row proceeds to the front row and at this time the return passage is full of empty sample vessels. As the sample vessels in the second front row are handled one by one, the sample vessels marshalled in the return passage are returned to the vacant back row one by one. The operation is continued until all the sample vessels initially placed in the back row of the waiting station 20 are returned to the original back row. However, the sample vessels whose treatment has finished are marshalled in the reversed order in a row.

Sequential operation of the above described apparatus can be controlled by the known technique of sequence control or by microcomputer and therefore it is not necessary to describe this aspect in detail.

Figure 10:
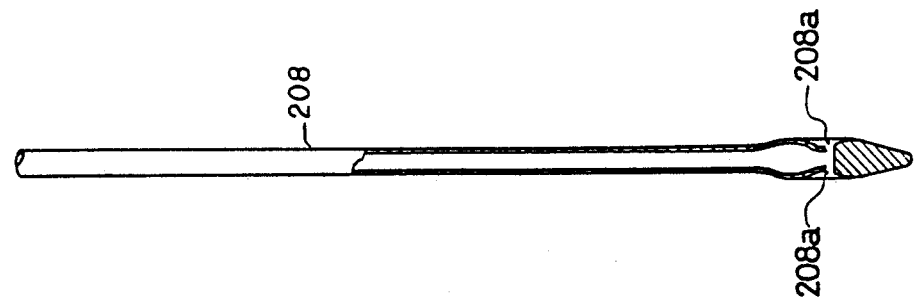
FIG. 10 is a cross-sectional view of the suction needle along the line X—X in FIG. 9.
Figure 9:
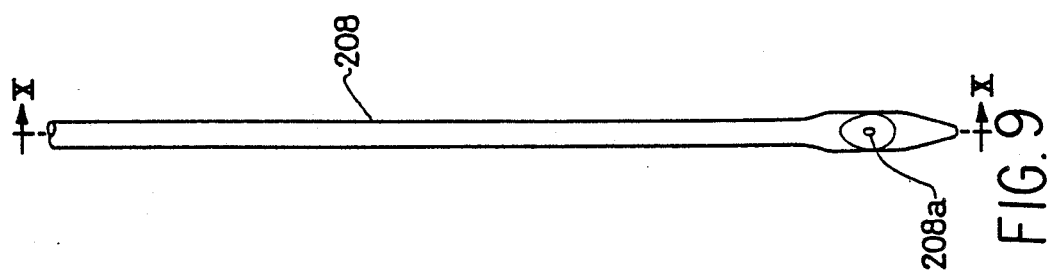
FIG. 9 is a side elevational view of a suction needle.

The suction needle used in the apparatus of the present invention preferably has an opening or openings at the side thereof as shown in FIGS. 9 and 10. This will prevent clogging of the opening with rubber debris, which might be formed when the needle penetrates the rubber stopper, and intrusion of any contaminants into the needle.

As described above, the automatic sampling apparatus of the present invention enables safe, rapid, accurate, systemmatic and wellordered handling of a number of stoppered sample vessesls with the stoppers retained. Therefore, contamination, deterioration, drying, etc. of the samples in the sample vessels during waiting for analysis is effectively prevented, and thus more accurate analysis is made possible. Also, samples which are easily vaporizable, give off toxic gases, etc. can be handled, and diffusion of gases, scattering of samples are prevented.

What is claimed as new and desired to be secured by Letters Patent of the United States is:

1. In an automatic sample supply apparatus which holds a plurality of sample vessels in a waiting station in a matrix pattern including a plurality of rows of sample vessels, and which sends out the sample vessels in the front row laterally one by one to a sampling station, returns the sample vessels which have finished the required treatment to the waiting station, and advances the sample vessels in a rearmost row in the waiting station collectively as a whole in one step one row at a time when all the sample vessels in the front row of the waiting station have been sent out, the improvement comprising the sampling station being provided with a suction needle assembly for sampling the sample in a sample vessel and which comprises a single needle for penetrating a stopper secured to the sample vessels and a holding block for said single needle.

2. The apparatus as claimed in claim 1, wherein said suction needle assembly comprises stopper means for preventing lifting of the sample vessel, wherein said stopper means is secured to the sample vessel and is held by said single suction needle.

3. The apparatus as claimed in claim 1 or 2, wherein said single suction needle has at least one suction hole on the side thereof.

4. The apparatus as claimed in claim 1, which further comprises a device for stirring the samples.

5. The apparatus as claimed in claim 1, wherein said holding block includes means for supplying a washing liquid to an outside portion of said single needle.

* * * * *